United States Patent [19]
Babcock et al.

[11] 3,988,194
[45] Oct. 26, 1976

[54] APPARATUS AND METHOD FOR APPLYING LABEL STOCK

[75] Inventors: Donald Babcock, Oak Lawn; Richard Modjeski, Evergreen Park; Perry Holman, Downers Grove, all of Ill.

[73] Assignee: Johnson & Johnson, New Brunswick, N.J.

[22] Filed: Jan. 27, 1975

[21] Appl. No.: 544,550

Related U.S. Application Data

[62] Division of Ser. No. 387,577, Aug. 10, 1973, Pat. No. 3,897,293.

[52] U.S. Cl. .............................. 156/459; 156/519; 156/552; 156/584
[51] Int. Cl.² ........................................ B32B 31/10
[58] Field of Search ........... 156/152, 199, 200, 201, 156/204, 227, 230, 254, 256, 264, 265, 289, 290, 292, 297, 299, 302, 344, 459, 461, 519, 520, 511, 542, 545, 552, 556, 568, 564; 128/156, 284, 287

[56] References Cited
UNITED STATES PATENTS

| 2,041,880 | 5/1936 | Valtat | 156/264 |
|---|---|---|---|
| 2,794,479 | 6/1957 | Ganz | 156/519 |
| 2,958,365 | 11/1960 | Molins et al. | 156/519 |
| 3,174,889 | 3/1965 | Anderson et al. | 156/254 |
| 3,221,738 | 12/1965 | Ekberg et al. | 156/290 |
| 3,322,600 | 5/1967 | Harrison et al. | 156/461 |
| 3,518,145 | 6/1970 | Christensen | 156/344 |
| 3,728,191 | 4/1973 | Wierzba et al. | 156/265 |
| 3,758,363 | 9/1973 | Frick | 156/552 |
| 3,776,234 | 12/1973 | Hoey | 128/287 |

Primary Examiner—Douglas J. Drummond
Assistant Examiner—John E. Kittle

[57] ABSTRACT

Tape tab fasteners are cut from a web stock, which includes a substrate coated on one surface with a pressure-sensitive adhesive and a release sheet positioned on the adhesive coating, and are applied transversely at predetermined intervals along the edge of a moving web of material, such as a web of plastic material suitable as an impervious barrier layer in disposable diapers. The web stock is drawn along a concave guide and a finger, positioned transversely between the substrate and release sheets, separates a predetermined width portion of the release sheet from the adhesive along one side of the web. The separated portion of the release sheet is folded over the remainder thereof. Tape tab fasteners of predetermined width are cut transversely from the end of the web stock and attached to the side edges of the moving web stock.

14 Claims, 4 Drawing Figures

APPARATUS AND METHOD FOR APPLYING LABEL STOCK

This is a division of application Ser. No. 387,577 filed Aug. 10, 1973 now U.S. Pat. No. 3,897,293.

BACKGROUND OF THE INVENTION

This invention relates to an applicator for pressure-sensitive adhesive fasteners and, more particularly, concerns a waist band fastener applicator for disposable diapers.

With the ever increasing acceptance of disposable diapers by consumers, and the corresponding increase in demand for such diapers, new materials and sophisticated manufacturing techniques and apparatus have been introduced to mass produce disposable diapers. Conventional disposable diapers are now provided with a fluid impervious backing sheet which eliminates the need for plastic or rubber pants and thus, increases the convenience in using such diapers. In recent years in order to further increase the convenience of disposable diapers as well as provide a safer means for fastening the diaper on an infant, pressure-sensitive adhesive fasteners have been substituted for the conventional safety pin.

Adhesive fasteners are usually supplied in pairs, one attached at each side portion of the water-impervious backing sheet near one end of the diaper so that as the diaper is conformed to an infant, a free end of each fastener may be attached to the corresponding opposite end of the diaper to secure about the infant. Various types of adhesive fasteners have been proposed in the past. In general, such adhesive fasteners are covered on their free adhesive ends by a release paper which is removed during the application of the diaper to the baby. The adhesive tape and the release paper are obtained during manufacture from separate rolls thereof. One method and apparatus for providing adhesive fasteners from separate rolls of adhesive tape and release paper is disclosed in Wierzba et al., U.S. Pat. No. 3,728,191, issued Apr. 17, 1973.

Label stock, a laminar assembly of a substrate and a release paper adhered to each other by an adhesive layer and wound together on a single roll, is more economical than conventional adhesive tape and release paper and this invention provides a suitable method and apparatus for utilizing label stock in the preparation of adhesive tabs for diapers.

SUMMARY OF THE INVENTION

The tape applicator of the present invention provides a novel method and apparatus for cutting and applying fasteners formed from label stock which is readily adaptable for mass-production of disposable diapers.

Label stock is produced in rolls and consists of a substrate which may be formed from various suitable materials. Label stock is made by coating a release paper with a tacky, pressure-sensitive adhesive layer and then covering the release paper with a substrate material. The latter material adheres to the pressure-sensitive material much more strongly than the release paper; and in any subsequent separation of the layers, the adhesive layer remains on the substrate.

The present invention is particularly adaptable for use with label stock having a substrate which possesses isotropic tensile strength so that re-orientation of the fasteners cut therefrom is eliminated. Substrates having maximum tensile strength in the transverse direction may also be utilized. One substrate which is substantially isotropic in tensile strength is formed by melt extruding polyethylene fibers in random orientation to form a continuous film having isotropic tensile strength.

The use of label stock by the method and apparatus of the present invention, as opposed to prior art pressure-sensitive adhesive fasteners, results in machinery and products savings due to the fact that the release sheet need only be as wide as the substrate since it is not necessary to accommodate for fluctuations in positioning. Since both the substrate and release sheet are positioned together, the release paper functions in effect as the sizing, as well as providing the release paper for use on the diaper.

The present invention is particularly adaptable for use on mass production lines for producing disposable diapers and may be positioned at any position along the production line wherein the impervious backing sheet is moving. Label stock of the type described above is unwound and payed out from a roll thereof and is conveyed along a concave arcuate guide member as a web with the release sheet facing upwardly. The label stock web moves past a stationary separation finger, introduced between the release sheet, and the adhesive layer along one side of the web to cause the release paper to separate at that side from the adhesive layer. As the web is conveyed along the arcuate guide, the separated release paper is directed into an overlying position onto the unattached portion of the release paper by means of a folding roller which is disposed at an angle to the movement of and in contact with the web. A guide plate complementary in shape with and positioned over the unattached portion of the release paper co-operates with the arcuate path defined by the guide and the roller to cause the separated release sheet to fold over the unattached release paper.

After the portion of the release paper has been folded over and creased so as to maintain the fold, the web is fed over a continuously moving vacuum wheel disposed adjacent the path of the water-impervious sheet. The label stock web is controlled by drive means upstream of the vacuum roller so that the vacuum roller may slip relative to the label stock web. A rotating cutter blade disposed adjacent the vacuum roller and driven in timed relationship with the movement of the water-impervious sheet cuts fasteners from the web which are carried by the vacuum roller into engagement with the water-impervious sheet in timed relationship with its movement in the production line. The uncovered adhesive coating of the fastener is adhered to the backing sheet to fasten the fastener thereon and separate from the vacuum roller. The fasteners are then carried along the production line with the impervious sheet for further processing and packaging.

Since fasteners are attached at both sides of the water-impervious sheet, two label stock applicator units, one for each side of the diaper web, are used in accordance with the present invention.

DETAILED DESCRIPTION OF A PREFERRED EMBODIMENT

Figure 1:
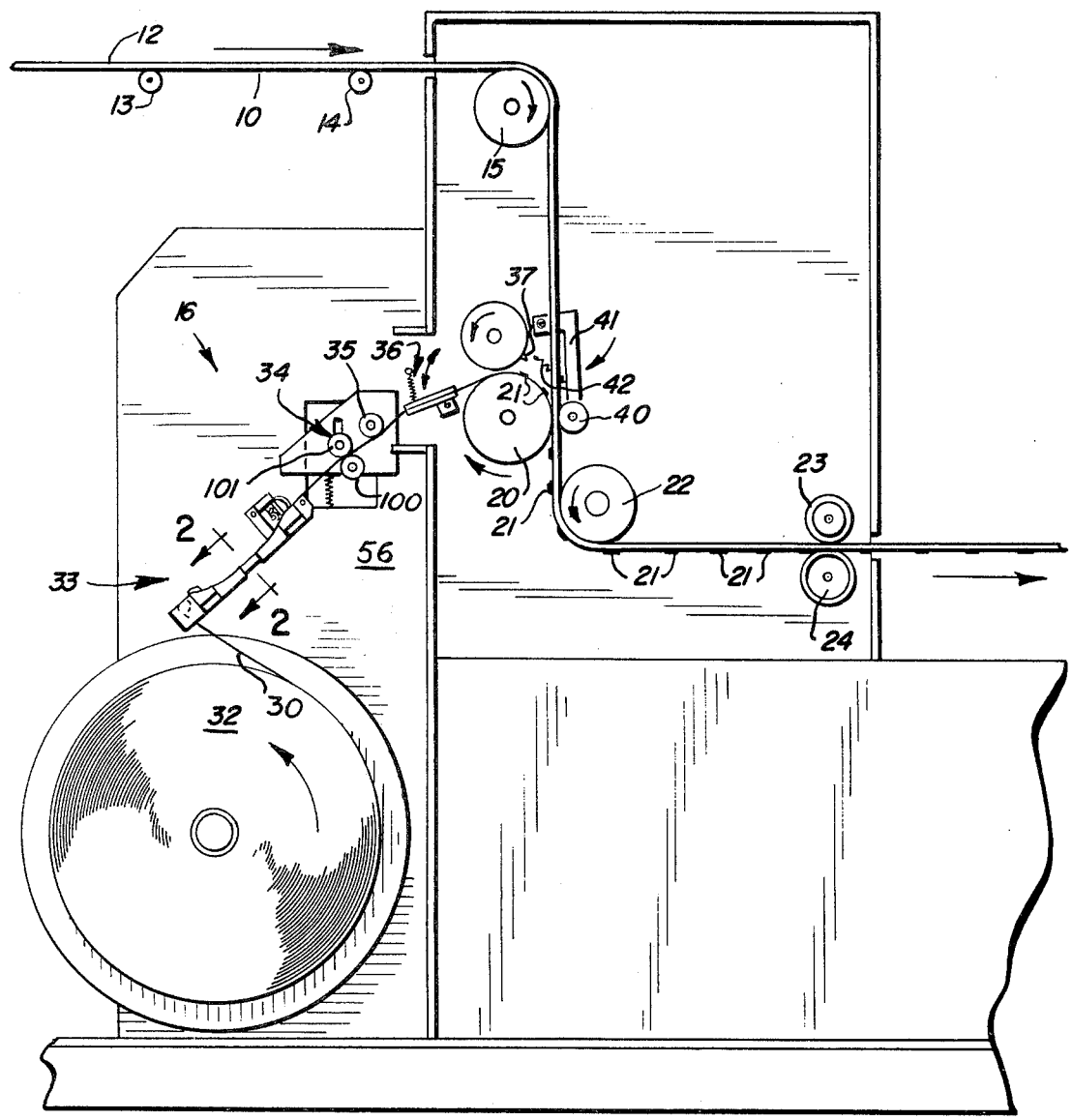
FIG. 1 is an elevational view of the apparatus in accordance with the present invention.

While this invention is susceptible of embodiment in many different forms, there is shown in the drawings and will herein be described in detail only a preferred embodiment of the invention, with the understanding that the present invention is to be considered as an exemplification of the principles of the invention and is not intended to limit the invention to the embodiments illustrated.

With reference to FIG. 1, the present invention is particularly adaptable for use in a mass production line for producing disposable diapers. The apparatus may be located at any position in the production line through which a continuous web 10 passes which will form the water-impervious backing sheet of the disposable diaper. As illustrated, web 10 has a web of absorbent material 12 positioned on one surface thereof and is being directed in the direction indicated on FIG. 1 along an elevated horizontal path defined by rollers 13 and 14 above the fastener applicator 16 of this invention. In a diaper having a separate facing layer and absorbent pad, both of these elements are glued to the upper face of web 10, as shown in the upper left of FIG. 1. The diaper stock web is then directed vertically downward around roller 15 to position the backing sheet in a vertical plane adjacent vacuum roller 20 which transfers fasteners 21 onto the backing sheet, as described in greater detail below. The diaper stock web is then directed horizontally by roller 22 and the web passes beneath two vertically disposed compression rollers 23 and 24 positioned adjacent each side of the diaper stock. The diaper stock then moves forwardly for further processing.

Label stock 30 is provided from a supply roll 32 and drawn through an inclined separator and folding mechanism 33 with the release sheet 30a facing upwardly which separates a predetermined width of release paper 30a above one edge from the adhesive coating on the substrate 30b to expose a portion of the coating for adherence to the backing sheet and folds over the separated portion of the release paper to provide a manually grippable portion for removing the release paper from the finished diaper during use.

Web 30 is drawn through mechanism 33 by a pair of drive rollers 34 positioned down-stream from mechanism 33 and which controls the advancement of the web during application to the backing sheet, as described in greater detail below.

After a portion of the release paper has been folded over, the web passes beneath a U-wrap tensioning roller 35 and through a spring loaded impact absorber mechanism 36 and about the top surface of the cylindrical vacuum roller 20. The movement of web 30 is controlled by the pair of drive rollers which advances a predetermined length of web beyond the point of tangency between vacuum roller 20 and cutter 37, disposed adjacent roller 20. The predetermined length corresponds in size to the width of the fastener to be formed. The advanced portion of the web overlying vacuum roller 20 is free to slip relative to the rotation of the vacuum roller so that a slip clutch effect is produced.

Cutter 37 operates in timed relationship with the movement of the diaper stock web so that fasteners 21 are cut from web 30, transferred by vacuum roller 20 into contact with the water impervious backing sheet, and adhered thereto at preselected intervals. Roller 20 is provided with a plurality of radially extending vacuum ports which receive vacuum from a suitable source to transfer fasteners 21 out from web 30 by rotating cutter 37 as well as tension the web downstream from the drive roller.

The fasteners utilized with the present apparatus have sufficient tack to adhere to the backing sheet and overcome the vacuum of roller 20 so that the fastener is carried along the process line by the backing sheet web. A compression roller 40 disposed in an overlying relationship to the point of attachment of the fasteners on the side of the diaper web stock is rotatably mounted at the free end of an inverted L-shaped bracket 41 which is pivotally attached to the machine frame at the other free end and biased into engagement with the diaper web stock by spring 42.

Since fasteners are applied on both side portions of a disposable diaper, it will be appreciated that a corresponding mechanism of the type to be described may be positioned in mirror image relationship thereto to provide fasteners to the other side of the diaper web stock. By virtue of the mirror image mounting the apparatus, different diaper widths may be readily accommodated by moving the fastener applicators horizontally relative to one another and corresponding to the change in width of the diaper to be produced.

Figure 3:
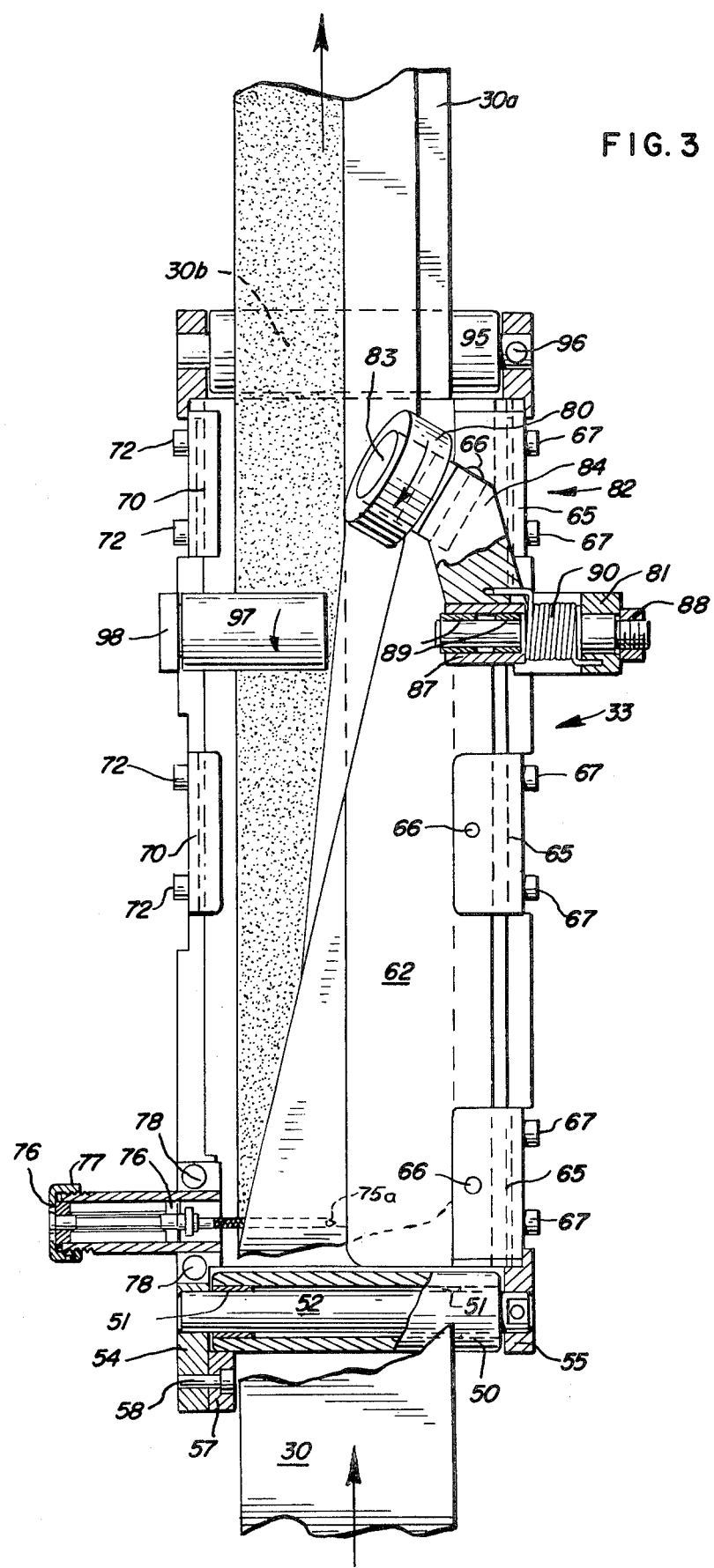
FIG. 3 is a plan view with certain portions in section of the separator and folding mechanism.
Figure 4:
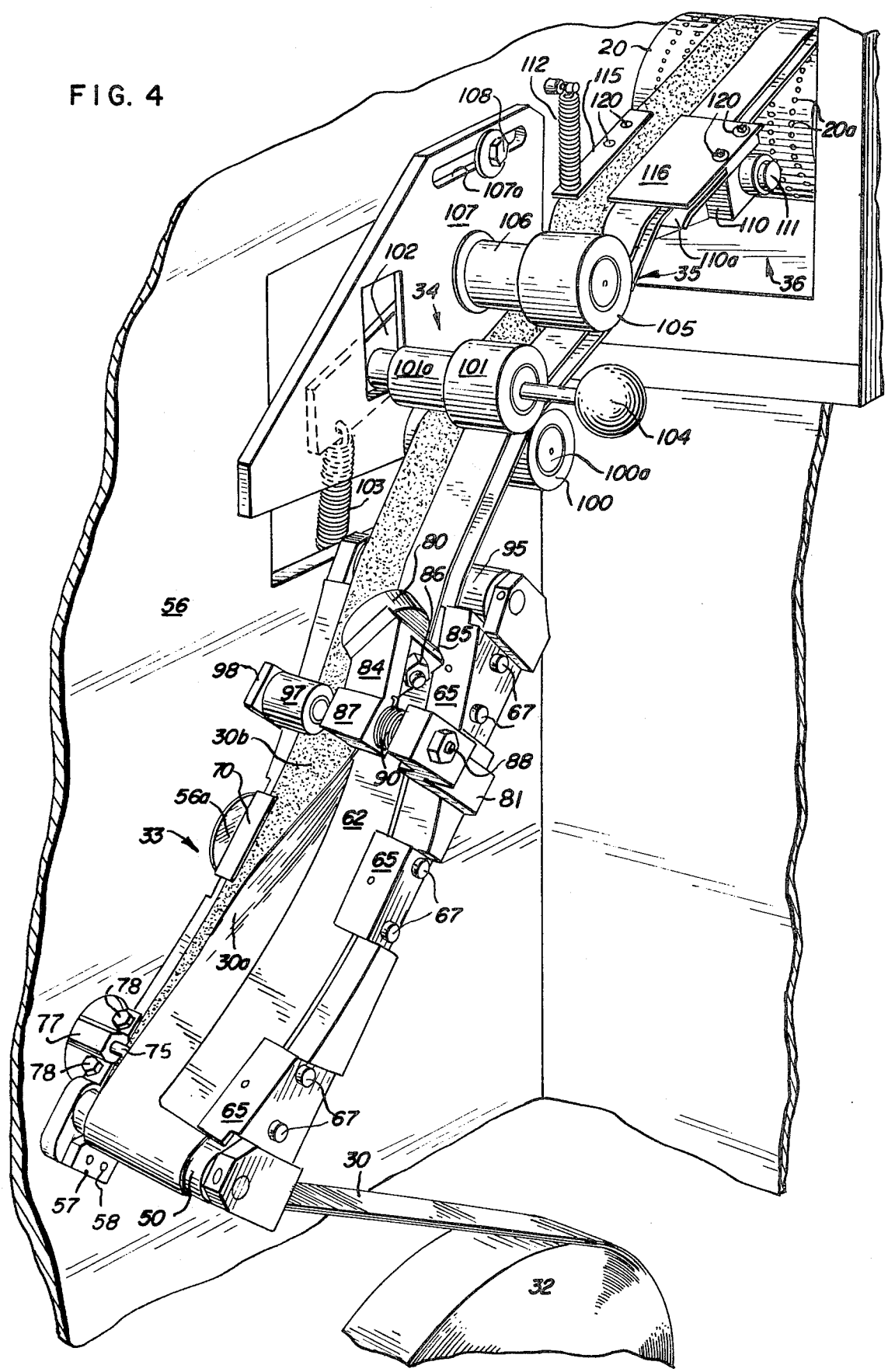
FIG. 4 is a perspective view of the apparatus of this invention.

Referring to FIGS. 3 and 4, label stock web 30 is fed upwardly from roll 32 about a U-wrap roller 50 which directs the web into separator and folding mechanism 33. Roller 50 is rotatably mounted by internal bearings 51 at each end thereof on a transversely disposed shaft 52. Shaft 52 extends between side plates 53 and 54 of the folding mechanism. Side plate 54 which is mounted to frame plates 56 by bracket 56a mounts, as by bolt 58, an arcuate shaped guide block 57, which is complementary in shape to roller 50. Block 57 provides a side guide portion 57a for directing web 30 into the folding mechanism 33.

Figure 2:
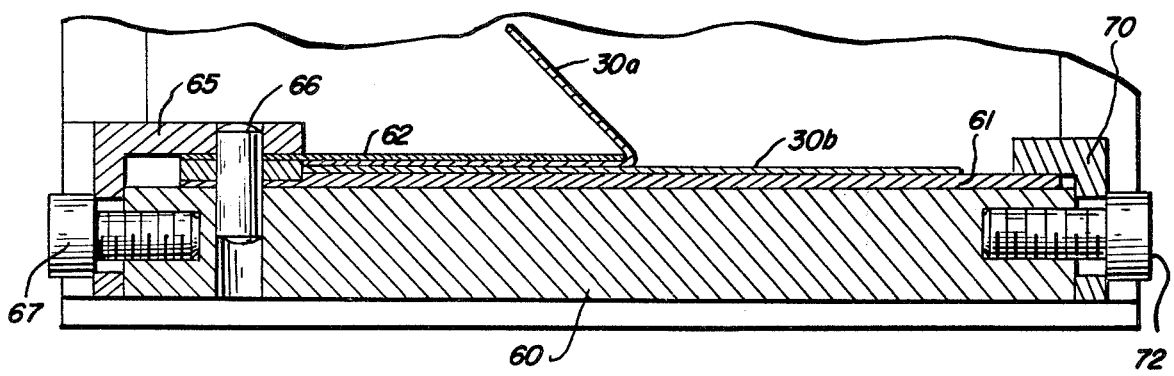
FIG. 2 is a section view taken along plane 2—2 on FIG. 1.

As the web is drawn through the folding mechanism by the pair of drive rollers 34, the web is directed along an inclined concave arcuate path defined by a concave base plate 60 located between plates 54 and 55, and which may be integrally formed therewith. The upper arcuate surface of base plate 60, FIG. 2, is provided with a Teflon plate 61 to permit easy sliding of the web thereon during the folding process.

Teflon plate 61 is mounted to base plate 60 by inverted, generally L-shaped, arcuate clamps 70 and bolts 72. The lower surface of the arcuate portions of clamps 70 bear against the upper surface of plate 61 and thus maintain the Teflon plate in contact with base plate 60.

An arcuate folder plate 62 complementary to the arcuate Teflon plate 61 is mounted thereabove along the side of the folder mechanism by inverted generally L-shaped clamps 65 and pins 66 to define a generally U-shaped path. Release paper 30a is folded about the free edge of plate 62, FIG. 2, as the web is carried along the folding mechanism. L-shaped clamps 65 are mounted on base plate 60 as by bolts 67. In order to assure that no sticking occurs between the web and the folder plate, it is preferred that the folder plate be coated with Teflon at all its working surfaces.

In order to separate the release sheet 30a from the adhesive coated substrate 30b, a separation finger 75, is positioned to extend inwardly from plate 54 between the release paper and substrate. Referring to FIG. 3, finger 75 is in the form of a slender knurled member having a conical point 75a, which extends transversely to the path of the web and is mounted on frame plate 54 at the elevation of the web by means of bearings 76 and housing 77. Housing 77 is secured to frame 54 by bolts 78. It will be appreciated that separation finger 75 is in contact with the adhesive surface of substrate 30b and therefore must be of a type which will not stick to the substrate or cause the release sheet to be ripped. It has been found desirable to utilize a knurled surface which provides a minimum contact area with the adhesive coated substrate. It is also preferred to use a separation finger which rotates in the direction of the web movement of the adhesive substrate, although other finger configurations may be used.

As the release sheet is separated from the substrate, it is directed beneath a folding roller 80 which is mounted for rotation at an angle to the path of the web and cooperates with folder plate 62 to initially fold the separated release sheet into overlying relationship with the folder plate. Roller 80 is mounted to side plate 55 adjacent the output portion of the folding mechanism by frame mounting bracket 81, and a spring biased mounting assembly 82. Mounting assembly 82 includes a roller axle 83 which mounts roller 80 to an angled support bracket 84. Bracket 84 is provided with a mounting flange 85, FIG. 4, at one end, by which roller axle 83 is mounted as by end bolt 86, and a mounting collar 87 at its opposite end. A stud shaft 88 extends transversely from bracket 81 to mount collar 87 thereon by means of bearings 89 so that angled brackets 84 may rotate thereabout. A torsion spring 90 is disposed between bracket 81 and angle support bracket 84 to bias roller 80 into engagement with the separated release sheets 30a, and the output end of folder plate 62. Roller 80 is preferably formed with a rubber working surface so that resilient engagement may be maintained with the release paper and thus assure proper folding thereof.

To prevent the uncovered portion of the substrate from being folded with the release sheet, a Teflon roller 97 is positioned to overlie and contact the exposed substrate. Roller 97 is rotatably mounted to frame member 54 by a generally L-shaped mounting bracket 98 positioned slightly upstream from roller 80.

After the release paper has been initially folded, the web passes over a second transversely disposed roller 95 which is mounted by shaft 96 in similar fashion to roller 50 to frame plates 54 and 55.

As indicated above, the web movement is controlled by a pair of drive rollers 34 which include a lower Teflon-coated drive roller 100 mounted on shaft 100a which receives power input (not shown) in timed relationship with the movement of the diaper web stock and which is geared to advance the label stock web at predetermined length corresponding to the width of the fasteners 21. In order to assure proper braking of the movement of the web, upper Teflon-coated roller 101 is rotatably mounted on shaft 101a of a lever mechanism 102 which is biased downwardly by spring 103 to maintain roller 101 into gripping engagement with roller 100. A handle 104 is provided outboard of roller 101 for lifting roller 101 during start-up and maintenance of the apparatus.

The web of label stock advanced by drive rollers 34 passes beneath tensioning roller 35 which includes a Teflon-coated cylindrical folding portion 105 which is rotatably mounted on shaft 106. Shaft 106 is fixedly positioned on a generally triangular shaped mounting plate 107 which may be moved horizontally relative to frame member 56 by guide slot 107a through which pass mounting bolt 108. Referring to FIG. 1, it will be observed that shaft 100a is also mounted on triangular shaped plate 107. Bracket 102 is rotatably mounted about a portion of shaft 106 extending beyond plate 107 so that the pair of drive rollers and the tensioning roller may be moved in unison in a horizontal plane for adjustment, as will be described below.

After the release paper has been finally folded by rollr 105, the web passes through impact absorber 36 positioned above the elevation of roller 105. Impact absorber 36 includes a generally flat base guide member 110 which is rotatably mounted to the machine frame by shaft 111 at its downstream portion so as to produce a lever. Guide member 110 is maintained in an inclined position by spring 112 which is attached at the upstream end of impact absorber 36 and to the machine frame at the other end. Guide member 110 is preferably Teflon-coated to provide easy slippage of the web thereon and includes a downwardly flared entrance lip 110a to assure easy entrance of the web. Two elongated guide members 115 and 116 are attached at the sides of guide member 110 in overlying relationship to the path of the web 30 as by bolts 120. Guide member 115 is Teflon-coated and positioned in overlying relationship to the exposed adhesive coated substrate 30b to cooperate with guide member 110 in guiding the web to vacuum roller 20. Guide member 116 is disposed in overlying relationship with the folded release sheet. Guides 115 and 116 are also preferably Teflon-coated to assure slippage of the web.

As the web passes from impact absorber 136 onto the vacuum roller 20, the advancement of the web is controlled by the pair of drive rollers so that the vacuum roller slips relative to the web as the roller 20 maintains tension in the web. Due to the tension in web 30, when a fastener is severed therefrom, a pulling effect will be generated in the web as the fastener is cut therefrom. Accordingly, to prevent the release sheet 30a from ripping during the folding operation or being pulled through the drive rollers when a fastener is cut the tensioning roller 105 is adjusted horizontally relative to impact absorber 36 to produce an S-Shape curve in the web. In this manner, as the web tension is increased during the cutting operation, the upstream end of the impact absorber will be pivoted downwardly, as indicated on FIG. 1, to take up the impact. Thus, by adjusting the position of plate 107, the loading impact on the absorber may be controlled and adjusted by the degree of S-wrapping.

As previously indicated, the apparatus as described includes a mirror image apparatus for applying fasteners to the other side of the diaper web stock and accordingly cutter 37 and vacuum wheel 20 may extend between the two label stock webs fed from the apparatus since the fasteners are positioned at the same relative location on the backing sheet.

As fasteners are cut from the web, they are carried by vacuum roller 20 by means of radially extending passage ways 20a which receive vacuum from a suitable source (not shown). As fasteners 21 are carried by vacuum roller 20, they are brought into contact with the impervious backing sheet 10 and are forced to adhere thereto by the adhesive coated substrate 30b under the influence of compression roller 40. Compression roller 40 may be of the type of individual rollers for each side of the diaper web or may be a continuous roll extending coterminously vacuum roll 20.

The diaper web with the fasteners attached thereto then passes beneath a second set of compression rollers 23 and 24 which may be individual rollers for each side of the diaper web or may be a continuous roller extending across the width of the diaper. When the apparatus is used with a diaper web on which the absorbent material has already been positioned, it is preferable that rollers 40 and 23 and 24 are individual rollers to prevent compression of the absorbent material which may be undesirable in the production of the diaper.

It should be pointed out, that by adjusting the drive to roller 100, or substituting a new roller with a larger diameter, the amount of web fed forwardly and correspondingly the width of the tab fastener cut from the web may be readily adjusted. Likewise, the width of the label stock 30 may be changed with a resulting requirement that the folder plate be adjusted in width to correspond to the unattached portion of the release sheet on the fasteners to be produced by the apparatus. These and other modifications of the present invention may be utilized by those skilled in the art without departing from the scope and spirit of the invention as pointed out in the appended claims.

What is claimed is:

1. Apparatus for providing adhesive tape tabs on a disposable diaper from a roll of a laminar assembly of a substrate material and a release sheet material held together by a layer of a tacky, pressure-sensitive adhesive which comprises: means for unwinding said roll and paying out said laminar assembly therefrom; means for separating an edge portion of said release sheet from said laminar assembly at an unwound portion thereof, concave folding means for folding back said separated portion of said release sheet into an overlying relationship to an unseparated portion thereof to thereby expose a portion of said adhesive layer as an adhesive coating on said substrate; means for severing end segments of said laminar assembly; and means for pressing said severed end segments against a moving web of water-impervious material at a marginal side portion thereof at intervals corresponding to diaper lengths to adhere said end segments to said web by said adhesive coating on said substrate.

2. Apparatus of claim 1 wherein said separating means includes a finger means adapted to be positioned between said release sheet and said substrate at one side edge of said laminar assembly at a payed out portion thereof, whereby said side edge is separated as said laminar assembly passes said finger means.

3. Apparatus of claim 2 wherein said finger means includes an elongated member extending transversely of said laminar assembly.

4. Apparatus of claim 3 wherein said finger means further includes means for rotatably mounting said elongated member, whereby said member is rotated under the influence of said pressure-sensitive adhesive as said laminar assembly passes said finger means.

5. Apparatus of claim 4 wherein said elongated member is knurled about the periphery thereof.

6. Apparatus of claim 1 wherein said folding means includes a generally concave support member adapted to position the non-adhesive coated surface of said substrate thereon; folding plate means disposed adjacent said support surface above the path of the unseparated portion of said release sheet; and means for drawing said separated portion of said release sheet about the inner edge of said folding plate means, whereby said separated portion is folded into overlying relation with the unseparated portion of said release sheet.

7. Apparatus of claim 6 wherein said folding plate means includes an arcuate, generally rectangular-shaped plate, said plate being complementary to said support member and extending inwardly of the laminar assembly path to about the line of separation of said release sheet whereby the inner edge of said member acts as a folding edge as said separated portion is drawn thereabout.

8. Apparatus of claim 7 wherein said drawing means includes roller means positioned adjacent the top surface of said plate at the downstream end thereof, said roller means including a roller, rotatably disposed at an acute angle to the path of said laminar assembly and means biasing said roller into engagement with said plate whereby said separated portion of the release material is folded as said laminar assembly is payed therebetween.

9. Apparatus of claim 8 wherein said roller is a rubber roller thereby to provide resilient engagement with said separated portion of said release sheet.

10. Apparatus of claim 1 wherein said unwinding and paying means includes power-driven roller means located downstream of said folding means.

11. Apparatus of claim 10 wherein said power-driven roller means includes means for synchronizing the advancement of said laminar assembly to said severing means thereby to control the size of said end segments severed from said laminar assembly.

12. Apparatus of claim 1 wherein said severing means includes a rotatable cutter and means for rotating said cutter into engagement with said laminar assembly to cut end segments therefrom in timed relationship to the movement of said water-impervious web; said pressing means includes a rotatable vacuum pickup roller disposed adjacent said cutter and said water-impervious web; said vacuum pickup roller is adapted to have the leading end of said laminar assembly positioned thereon and means for continuously rotating said vacuum pickup roller to produce a slip clutch effect between said vacuum pickup roller and said laminar assembly thereby to tension said laminar assembly; and means is provided for advancing said laminar assembly beyond the nip of said cutter and said vacuum pickup roller to provide end segments of predetermined length, said vacuum pickup roller being adapted to carry said severed end segments into engagement with said water-impervious web and hold them thereon until the adherence of said tape tab overcomes the suction of said vacuum roller.

13. Apparatus of claim 12 further including means for absorbing tension impact loading on said laminar assembly as end segments are severed therefrom.

14. Apparatus for providing adhesive tape tabs on a disposable diaper from a roll of a laminar assembly of a substrate material and a release sheet material held together by a layer of tacky, pressure-sensitive adhesive, said roll having a width corresponding to the length of said tape tabs, which comprises: power-driven roller means adapted to unwind said roll and pay out said laminar assembly therefrom; separating and folding means located upstream of said power-driven rollers at an unwound portion of said laminar assembly including an upwardly inclined concave support member adapted to position the non-adhesive coated surface of said substrate thereon with the release sheet facing upwards; a knurled, elongated finger, means for rotatably mounting said finger transversely at one side of said support member at the input end thereof, said finger adapted to be positioned between said release sheet and said substrate to cause separation of an edge portion therebetween; a generally rectangular arcuate shape folding plate, complementary to the curvature of said support member; means mounting said plate in juxtaposition with the top surface of said support member on the side opposite said finger, the inner edge of said plate defining a folding edge for said release sheet; a resilient roller; means biasing said roller into engagement with said plate adjacent the output end of said support member, said roller being disposed at an acute angle to the path of said laminar assembly thereby to draw the separated portion of said release sheet about said inner edge of said plate and into overlying relationship with the unseparated portion thereof; means located downstream from said power-driven roller including a rotatable cutter disposed above the path of said laminar assembly; means for rotating said cutter into engagement with said laminar assembly to cut end segments therefrom in timed relationship to the movement of a web of water-impervious material; a rotatable vacuum pickup roller disposed adjacent said cutter and said water-impervious web; said vacuum pickup roller adapted to have the leading end of said laminar assembly positioned thereon; means for continuously rotating said vacuum pickup roller to produce a slip clutch effect between said vacuum pickup roller and said laminar assembly thereby to tension said laminar assembly, said power-driven rollers adapted to advance said laminar assembly beyond the nip of said cutter and said vacuum pickup roller to produce end segments of predetermined length, said vacuum pickup roller adapted to carry severed end segments of said laminar assembly into engagement with said water-impervious web and hold them thereon until the adherence of said tape tab to said water-impervious web overcomes the suction of said vacuum roller; and means located between said power-driven rollers and said vacuum pickup roller for absorbing tension impact loading on said laminar assembly as end segments are severed therefrom.

* * * * *